US008150509B2

(12) United States Patent
Kadhiresan et al.

(10) Patent No.: US 8,150,509 B2
(45) Date of Patent: Apr. 3, 2012

(54) SYSTEMS AND METHODS FOR DRUG THERAPY ENHANCEMENT USING EXPECTED PHARMACODYNAMIC MODELS

(75) Inventors: Veerichetty Kadhiresan, Centerville, MN (US); Marina V. Brockway, Shoreview, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1024 days.

(21) Appl. No.: 10/970,449

(22) Filed: Oct. 21, 2004

(65) Prior Publication Data

US 2006/0089592 A1 Apr. 27, 2006

(51) Int. Cl.
*A61N 1/00* (2006.01)

(52) U.S. Cl. .......................................... 607/4; 128/923
(58) Field of Classification Search ................ 607/62, 607/4
See application file for complete search history.

(56) References Cited

U.S. PATENT DOCUMENTS

| 4,527,568 | A | * | 7/1985 | Rickards ................ 607/25 |
|---|---|---|---|---|
| 4,561,443 | A | | 12/1985 | Hogrefe et al. |
| 4,658,831 | A | | 4/1987 | Reinhard et al. |
| 4,674,652 | A | | 6/1987 | Aten et al. |
| 4,681,111 | A | | 7/1987 | Silvian |
| 4,705,043 | A | | 11/1987 | Imran |
| 4,757,816 | A | | 7/1988 | Ryan et al. |
| 4,793,353 | A | | 12/1988 | Borkan |
| 4,809,697 | A | | 3/1989 | Causey, III et al. |
| 4,911,327 | A | | 3/1990 | Shepard et al. |
| 4,932,408 | A | | 6/1990 | Schaldach |
| 4,947,407 | A | | 8/1990 | Silvian |
| 4,969,464 | A | | 11/1990 | Callaghan et al. |
| 5,058,581 | A | | 10/1991 | Silvian |
| 5,081,987 | A | | 1/1992 | Nigam |
| 5,088,056 | A | | 2/1992 | McIntosh et al. |
| 5,113,869 | A | | 5/1992 | Nappholz et al. |
| 5,117,825 | A | | 6/1992 | Grevious |
| 5,137,022 | A | | 8/1992 | Henry |
| 5,241,961 | A | | 9/1993 | Henry |
| 5,292,343 | A | | 3/1994 | Blanchette et al. |
| 5,331,966 | A | | 7/1994 | Bennett et al. |
| 5,336,245 | A | | 8/1994 | Adams et al. |
| 5,347,453 | A | | 9/1994 | Maestre |
| 5,350,411 | A | | 9/1994 | Ryan et al. |

(Continued)

FOREIGN PATENT DOCUMENTS

EP        0 554 955 A1    8/1993

OTHER PUBLICATIONS

U.S. Appl. No. 10/787,045, "Advanced Patient and Medication Therapy Management System and Method," filed Feb. 25, 2004.

(Continued)

*Primary Examiner* — Eric D. Bertram
(74) *Attorney, Agent, or Firm* — Schwegman, Lundberg & Woessner, P.A.

(57) ABSTRACT

A system or method including a device configured to measure at least one pharmacological effect of a drug on a patient. The measured pharmacological effect is compared to an expected pharmacodynamic model. The system can allow for real-time monitoring of positive and side-effects of drugs as well as drug resistance to optimize individual therapy. The system can also enable patient compliance monitoring.

24 Claims, 10 Drawing Sheets

U.S. PATENT DOCUMENTS

| | | | |
|---|---|---|---|
| 5,381,798 A | 1/1995 | Burrows |
| 5,383,915 A | 1/1995 | Adams |
| 5,390,238 A | 2/1995 | Kirk et al. |
| 5,413,594 A | 5/1995 | Williams |
| 5,415,181 A | 5/1995 | Hogrefe et al. |
| 5,416,695 A | 5/1995 | Stutman et al. |
| 5,458,122 A | 10/1995 | Hethuin |
| 5,476,485 A | 12/1995 | Weinberg et al. |
| 5,481,262 A | 1/1996 | Urbas et al. |
| 5,495,961 A | 3/1996 | Maestre |
| 5,509,927 A | 4/1996 | Epstein et al. |
| 5,522,865 A | 6/1996 | Schulman et al. |
| 5,549,654 A | 8/1996 | Powell |
| 5,576,952 A | 11/1996 | Stutman et al. |
| 5,626,630 A | 5/1997 | Markowitz et al. |
| 5,629,678 A | 5/1997 | Gargano et al. |
| 5,630,836 A | 5/1997 | Prem et al. |
| 5,646,912 A | 7/1997 | Cousin |
| 5,674,249 A | 10/1997 | de Coriolis et al. |
| 5,683,432 A | 11/1997 | Goedeke et al. |
| 5,713,937 A | 2/1998 | Nappholz et al. |
| 5,716,382 A | 2/1998 | Snell |
| 5,720,770 A | 2/1998 | Nappholz et al. |
| 5,722,999 A | 3/1998 | Snell |
| 5,724,580 A | 3/1998 | Levin et al. |
| 5,741,315 A | 4/1998 | Lee et al. |
| 5,743,267 A | 4/1998 | Nikolic et al. |
| 5,752,621 A | 5/1998 | Passamante |
| 5,752,976 A | 5/1998 | Duffin et al. |
| 5,752,977 A | 5/1998 | Grevious et al. |
| 5,759,199 A | 6/1998 | Snell et al. |
| 5,766,232 A | 6/1998 | Grevious et al. |
| 5,769,876 A | 6/1998 | Silvian |
| 5,772,586 A | 6/1998 | Heinonen et al. |
| 5,774,501 A | 6/1998 | Halpern et al. |
| 5,791,342 A | 8/1998 | Woodard |
| 5,792,207 A | 8/1998 | Dietrich |
| 5,814,089 A | 9/1998 | Stokes et al. |
| 5,836,983 A | 11/1998 | Weijand et al. |
| 5,843,133 A | 12/1998 | Routh et al. |
| 5,843,139 A | 12/1998 | Goedeke et al. |
| 5,861,014 A | 1/1999 | Familoni |
| 5,861,018 A | 1/1999 | Feierbach |
| 5,862,803 A | 1/1999 | Besson et al. |
| 5,889,474 A | 3/1999 | La Due |
| 5,899,928 A | 5/1999 | Sholder et al. |
| 5,899,931 A | 5/1999 | Deschamp et al. |
| 5,917,414 A | 6/1999 | Oppelt et al. |
| 5,919,214 A | 7/1999 | Ciciarelli et al. |
| 5,935,078 A | 8/1999 | Feierbach |
| 5,944,659 A | 8/1999 | Flach et al. |
| 5,957,861 A | 9/1999 | Combs et al. |
| 5,999,857 A | 12/1999 | Weijand et al. |
| 6,055,506 A | 4/2000 | Frasca, Jr. |
| 6,083,248 A | 7/2000 | Thompson |
| 6,093,146 A | 7/2000 | Filangeri |
| 6,115,636 A | 9/2000 | Ryan |
| 6,141,584 A | 10/2000 | Rockwell et al. |
| 6,169,707 B1 | 1/2001 | Newland |
| 6,170,488 B1 | 1/2001 | Spillman, Jr. et al. |
| 6,171,237 B1 | 1/2001 | Avitall et al. |
| 6,171,264 B1 | 1/2001 | Bader |
| 6,185,452 B1 | 2/2001 | Schulman et al. |
| 6,200,264 B1 | 3/2001 | Satherley et al. |
| 6,203,495 B1 | 3/2001 | Bardy |
| 6,206,835 B1 | 3/2001 | Spillman, Jr. et al. |
| 6,208,894 B1 | 3/2001 | Schulman et al. |
| 6,213,942 B1 | 4/2001 | Flach et al. |
| 6,216,038 B1 | 4/2001 | Hartlaub et al. |
| 6,221,011 B1 | 4/2001 | Bardy |
| 6,223,083 B1 | 4/2001 | Rosar |
| 6,234,343 B1 | 5/2001 | Papp |
| 6,236,889 B1 | 5/2001 | Soykan et al. |
| 6,240,317 B1 | 5/2001 | Villaseca et al. |
| 6,249,705 B1 | 6/2001 | Snell |
| 6,250,309 B1 | 6/2001 | Krichen et al. |
| 6,261,230 B1 | 7/2001 | Bardy |
| 6,263,245 B1 | 7/2001 | Snell |
| 6,263,246 B1 | 7/2001 | Goedeke et al. |
| 6,263,247 B1 | 7/2001 | Mueller et al. |
| 6,263,259 B1 | 7/2001 | Bartur |
| 6,289,238 B1 | 9/2001 | Besson et al. |
| 6,292,698 B1 | 9/2001 | Duffin et al. |
| 6,294,999 B1 | 9/2001 | Yarin et al. |
| 6,295,466 B1 | 9/2001 | Ishikawa et al. |
| 6,298,271 B1 | 10/2001 | Weijand |
| 6,300,903 B1 | 10/2001 | Richards et al. |
| 6,302,844 B1 | 10/2001 | Walker et al. |
| 6,304,788 B1 | 10/2001 | Eady et al. |
| 6,312,378 B1 | 11/2001 | Bardy |
| 6,319,200 B1 | 11/2001 | Lai et al. |
| 6,329,929 B1 | 12/2001 | Weijand et al. |
| 6,331,160 B1 | 12/2001 | Bardy |
| 6,336,903 B1 | 1/2002 | Bardy |
| 6,345,203 B1 | 2/2002 | Mueller et al. |
| 6,349,234 B2 | 2/2002 | Pauly et al. |
| 6,363,282 B1 | 3/2002 | Nichols et al. |
| 6,368,284 B1 | 4/2002 | Bardy |
| 6,398,728 B1 | 6/2002 | Bardy |
| 6,411,840 B1 | 6/2002 | Bardy |
| 6,418,346 B1 | 7/2002 | Nelson et al. |
| 6,438,407 B1 | 8/2002 | Ousdigian et al. |
| 6,442,432 B2 | 8/2002 | Lee |
| 6,442,433 B1 | 8/2002 | Linberg |
| 6,463,328 B1 * | 10/2002 | John ............................ 607/45 |
| 6,471,645 B1 | 10/2002 | Warkentin et al. |
| 6,477,424 B1 | 11/2002 | Thompson et al. |
| 6,480,745 B2 | 11/2002 | Nelson et al. |
| 6,599,281 B1 * | 7/2003 | Struys et al. .................. 604/503 |
| 6,635,014 B2 | 10/2003 | Starkweather et al. |
| 6,735,630 B1 | 5/2004 | Gelvin et al. |
| 6,824,512 B2 | 11/2004 | Warkentin et al. |
| 2001/0011153 A1 | 8/2001 | Bardy |
| 2001/0012955 A1 | 8/2001 | Goedeke et al. |
| 2001/0021801 A1 | 9/2001 | Bardy |
| 2001/0023360 A1 | 9/2001 | Nelson et al. |
| 2001/0025137 A1 | 9/2001 | Webb et al. |
| 2001/0025138 A1 | 9/2001 | Bardy |
| 2001/0025189 A1 | 9/2001 | Haueter et al. |
| 2001/0027331 A1 | 10/2001 | Thompson |
| 2001/0027349 A1 | 10/2001 | Eady et al. |
| 2001/0029321 A1 | 10/2001 | Beetz et al. |
| 2001/0031998 A1 | 10/2001 | Nelson et al. |
| 2001/0037056 A1 | 11/2001 | Nunome |
| 2001/0039372 A1 | 11/2001 | Yasushi et al. |
| 2001/0039375 A1 | 11/2001 | Lee et al. |
| 2001/0044588 A1 | 11/2001 | Mault |
| 2001/0047125 A1 | 11/2001 | Quy |
| 2001/0049554 A1 | 12/2001 | Ruiz et al. |
| 2001/0051764 A1 | 12/2001 | Bardy |
| 2001/0051765 A1 | 12/2001 | Walker et al. |
| 2001/0051787 A1 | 12/2001 | Haller et al. |
| 2002/0013517 A1 | 1/2002 | West et al. |
| 2002/0013518 A1 | 1/2002 | West et al. |
| 2002/0013538 A1 | 1/2002 | Teller |
| 2002/0013613 A1 | 1/2002 | Haller et al. |
| 2002/0013614 A1 | 1/2002 | Thompson |
| 2002/0019584 A1 | 2/2002 | Schulze et al. |
| 2002/0019586 A1 | 2/2002 | Teller et al. |
| 2002/0022776 A1 | 2/2002 | Bardy |
| 2002/0026103 A1 | 2/2002 | Norris et al. |
| 2002/0026104 A1 | 2/2002 | Bardy |
| 2002/0028988 A1 | 3/2002 | Suzuki et al. |
| 2002/0032470 A1 | 3/2002 | Linberg |
| 2002/0040234 A1 | 4/2002 | Linberg |
| 2002/0052539 A1 | 5/2002 | Haller et al. |
| 2002/0072785 A1 | 6/2002 | Nelson et al. |
| 2002/0082665 A1 | 6/2002 | Haller et al. |
| 2002/0087115 A1 | 7/2002 | Hartlaub |
| 2002/0095196 A1 | 7/2002 | Linberg |
| 2004/0127958 A1 * | 7/2004 | Mazar et al. .................... 607/60 |

OTHER PUBLICATIONS

U.S. Appl. No. 10/970,286, "Inregrated Pharmaceutical Dispensing and Patient Management Monitoring," filed Ocotber 21, 2004.

* cited by examiner

SYSTEMS AND METHODS FOR DRUG THERAPY ENHANCEMENT USING EXPECTED PHARMACODYNAMIC MODELS

CROSS REFERENCE TO RELATED APPLICATIONS

This application is related to U.S. patent application Ser. No. 10/970,286, filed Oct. 21, 2004, and entitled "Integrated Pharmaceutical Dispensing and Patient Management Monitoring," which is hereby incorporated by reference in its entirety.

TECHNICAL FIELD

The present invention generally relates to monitoring a pharmacological effect of a drug on a patient and, more specifically, to systems and methods for measuring data associated with a pharmacological effect of a drug on a patient and comparison of that data to an expected pharmacodynamic model.

BACKGROUND OF THE INVENTION

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, COPD, chronic pain, and epilepsy, is event driven, where acute de-compensations result in hospitalization.

In addition to causing considerable physical and emotional trauma to the patient and family, hospitalizations consume a majority of the total health care expenditure allocated to the treatment of heart failure. Hospitalization and treatment for an acute de-compensation typically occurs after the de-compensation event has occurred. However, most heart failure patients exhibit prior non-traumatic symptoms, such as steady weight gain, in the weeks or days prior to the de-compensation. If the caregiver is aware of these symptoms, it is possible to intervene before the event, at substantially less cost to the patient and the health care system.

Intervention is usually in the form of a re-titration of the patient's drug cocktail, reinforcement of the patient's compliance with the prescribed drug regimen, or acute changes to the patient's diet and exercise. Such intervention is usually effective in preventing the de-compensation episode and thus avoiding hospitalization. Patients with chronic heart disease can receive implantable cardiac devices such as pacemakers, implantable cardioverter defibrillators (ICDs), and heart failure cardiac resynchronization therapy (CRT) devices. Currently, the electrophysiologist that implants pacemakers and ICDs requires their patients to make clinic visits periodically, usually once every three or four months, in order to verify if their implanted device is working correctly and programmed optimally. Device follow-ups are usually performed by the nurse-staff assisted by the sales representative from the device manufacturers. Device follow-ups are labor intensive and typically require patients to make multiple clinic visits.

The data the caregiver does receive regarding a patient requires the caregiver to analyze the data and provide predictive and post-event diagnosis based on the data. However, as the amount of data collected regarding a particular patient increases, it becomes more difficult for a caregiver to assimilate and provide a meaningful analysis of all of the data. In addition, it is difficult for a caregiver to identify trends and other information from particular patients and leverage this knowledge for the treatment of larger populations.

It would therefore be desirable to develop an automated system to collect data regarding the physiological condition of a patient and to automate the process of analyzing the data.

SUMMARY OF THE INVENTION

The present invention generally relates to monitoring a pharmacological effect of a drug on a patient and, more specifically, to systems and methods for measuring data associated with a pharmacological effect of a drug on a patient and comparison of that data to an expected pharmacodynamic model.

In accordance with one aspect, the invention relates to an advanced patient management system includes a device configured to measure at least one pharmacological effect of a drug on a patient, a repeater unit in communication with the device and a network, and a host in communication with the device through the network and the repeater, the host including a database module and an analysis module. The database module stores data from the device measuring the pharmacological effect on the patient, and the analysis module compares the data to an expected pharmacodynamic model.

In accordance with another aspect, the invention relates to a method of enhancing drug therapy, including: measuring data associated with at least one pharmacological effect of a drug on a patient; communicating the data to a host; and comparing the data to an expected pharmacodynamic model.

The above summary is not intended to describe each disclosed embodiment or every implementation of the present invention. Figures and the detailed description that follow more particularly exemplify embodiments of the invention. While certain embodiments will be illustrated and described, the invention is not limited to use in such embodiments.

BRIEF DESCRIPTION OF THE DRAWINGS

The invention can be more completely understood in consideration of the following detailed description of various embodiments of the invention in connection with the accompanying drawings, in which.

Figure 1:
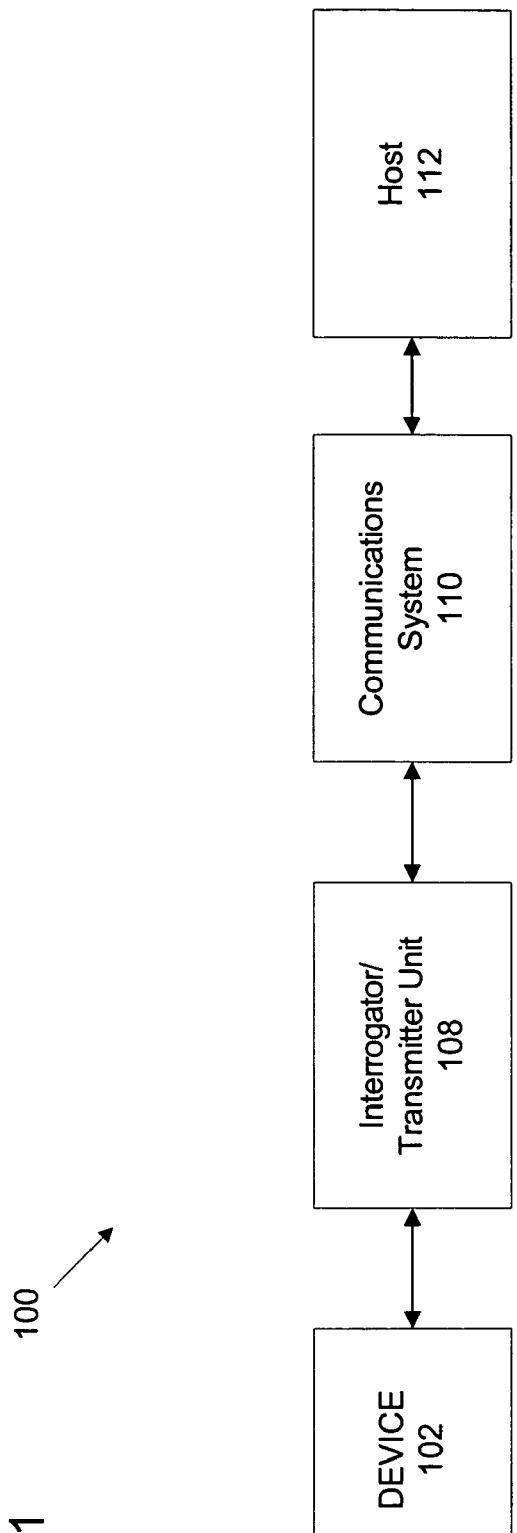
FIG. 1 illustrates another example system made in accordance with the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention generally relates to monitoring a pharmacological effect of a drug on a patient. More specifically, the present invention relates to systems and methods for measuring data associated with a pharmacological effect of a drug on a patient and comparison of that data to an expected pharmacodynamic model. Based on this comparison, one or more actions can be performed including, but not limited to, reporting, alarming, creation of new pharmacodynamic models, etc.

As used herein, the term "patient" is used to mean any individual from whom information is collected. The term "caregiver" is used herein to mean any provider of services, such as health care providers including, but not limited to, nurses, doctors, and other health care provider staff. The term "pharmacological effect" is used herein to describe any physiological or subjective response by a patient to a drug. The term "pharmacokinetics" is used herein to mean the absorption, distribution, metabolism and elimination of a drug by a patient's body. The term "pharmacodynamic" is used herein to describe biochemical and physiological effects of a drug and its mechanism of action.

I. Therapy Enhancement Using Expected Pharmacodynamic Models

In illustrated embodiments, therapy for a patient can be enhanced using data collected by one or more devices associated with a patient. Specifically, one or more sensors are used to collect data associated with the pharmacological effects of a drug taken by the patient. The collected data is compared to an expected pharmacodynamic model. Based on this comparison, one or more actions are performed including, but not limited to, reporting, alarming, creation of new pharmacodynamic models, etc.

Referring now to FIG. 1, an example system 100 for collecting and analyzing patient data is illustrated. System 100 includes a device 102, an interrogatory/transceiver unit (ITU) 108, a communications system 110, and a host 112.

Device 102 is a sensor that can measure a pharmacological effect (e.g., physiological or subjective) of a drug on a patient. Device 102 can be configured in a manner similar to that of devices 602, 604, 606, 902, 903, 904, and 906 described below. For example, device 102 can be an implanted device such as, for example, a cardiac rhythm management (CRM) device including a pacemaker, a cardioverter defibrillator, and a heart failure cardiac resynchronization therapy device. The device 102 can also be a non-implanted device such as, for example and without limitation, a scale, a blood pressure cuff, blood content monitor (i.e., gases, glucose, creatinine, BNP), etc. Device 102 can collect data associated with the patient including, but not limited to, activity level, weight, intracardiac or systemic blood pressure, heart rate, heart rate variability, thoracic impedance, heart sounds, etc.

Device 102 generally collects data associated with the patient and communicates the data to host 112. In one embodiment, the device 102 communicates with host 112 through ITU 108 and communications system 110. Other configurations are also possible. For example, in some embodiments, device 102 can communicate directly with communications system 110 and/or host 112. In the illustrated embodiment, device 102 can upload collected data to ITU 108 in real-time, on a periodic (batch) basis, or manually such as when interrogated by the ITU 108.

Figure 2:
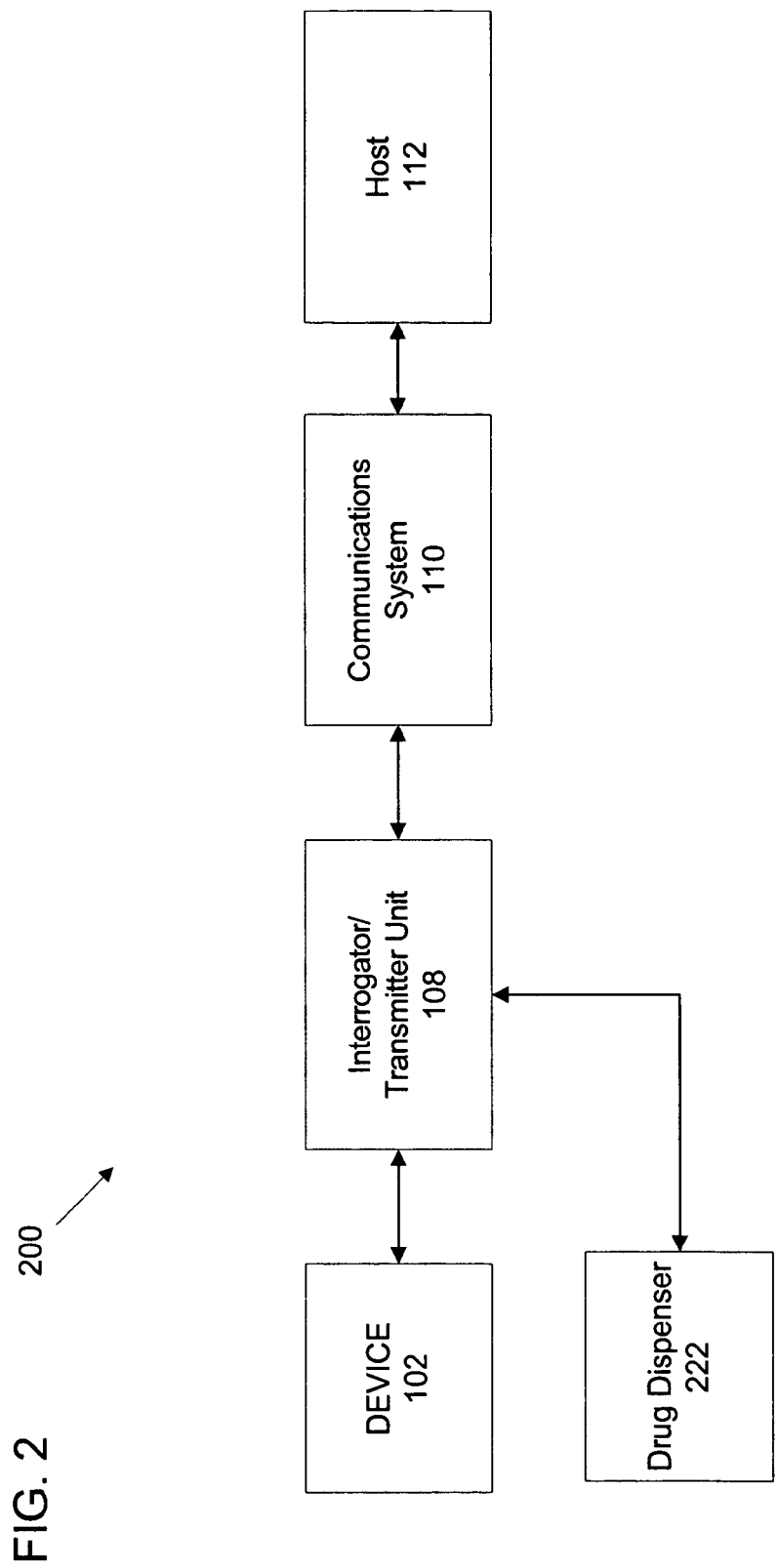
FIG. 2 illustrates another example system made in accordance with the present invention.

Referring now to FIG. 2, another example system 200 is illustrated. System 200 is similar to system 100 described above, except that system 200 also includes a drug dispenser 222. The drug dispenser 222 can be configured in a manner similar to drug dispenser 902 described below. For example, the drug dispenser 222 can be a dispenser that dispenses a drug to a patient so that the patient can administer the drug at given times in certain amounts. In other embodiments, the drug dispenser can be an implanted or external device (e.g., drug pump) that dispenses a certain amount of one or more drugs to a patient at periodic intervals or at times when a monitored state of the patient dictates dispensing of the drug or drugs.

The drug dispenser 222 can communicate information associated with the dispensing of drugs to the patient including, but not limited to, dispense date, dispense time, and amount/type of drug dispensed. Based on the data communicated by device 102 and/or drug dispenser 222, therapy for a patient can be enhanced.

Figure 3:
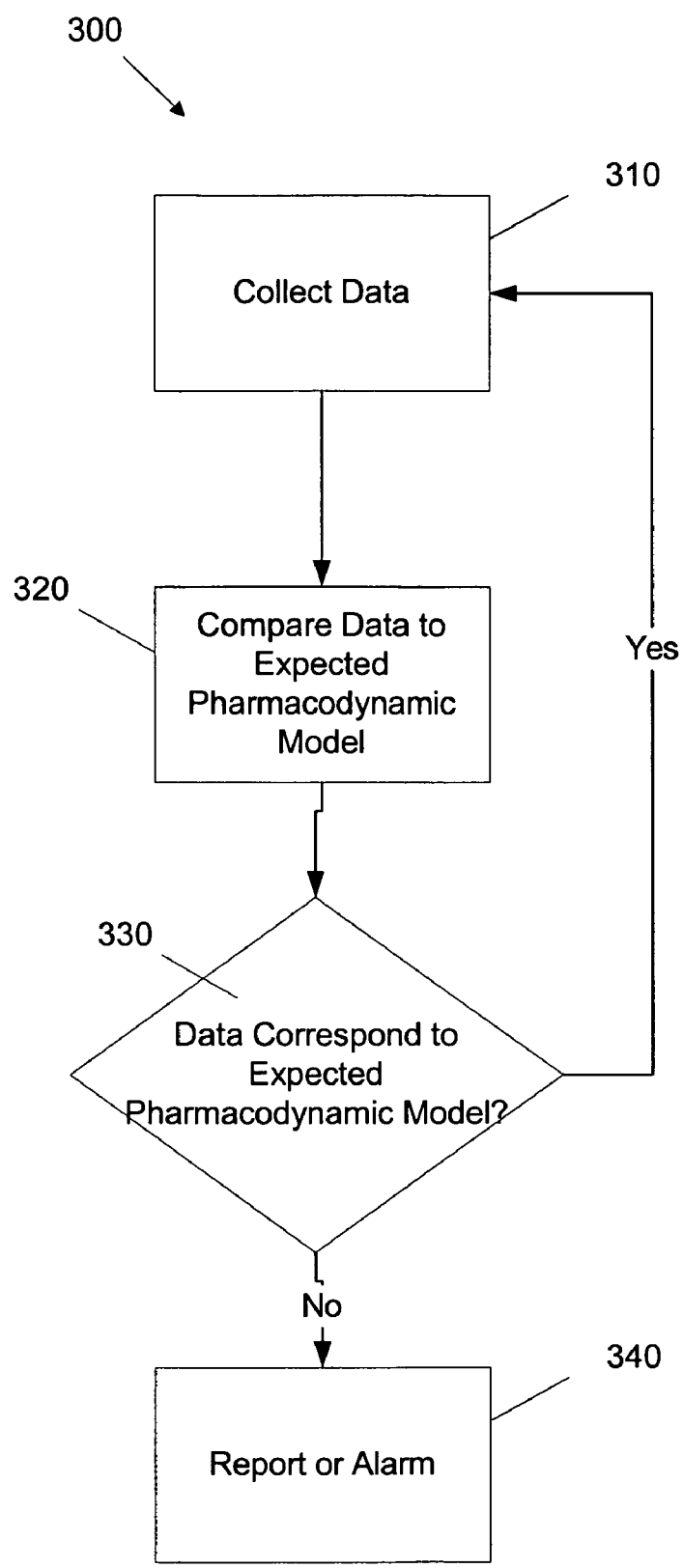
FIG. 3 illustrates an example method for collection and analysis of a pharmacological effect of a drug on a patient.

Referring now to FIG. 3, a flow diagram 300 illustrates one example method for enhancing therapy for a patient. In operation 310, data is collected from the patient using, for example, device 102 and/or drug dispenser 222. This data can include, for example, the pharmacological effect(s) of one or more drugs on the patient.

Next, in operation 320, the collected data is compared to an expected pharmacodynamic model (see FIGS. 4 and 5 described below). The expected pharmacodynamic model can be selected in various ways. For example, the model can be selected based on population statistics arranged, for example, according to age, race, national origin, and/or gender. In other examples, the model can be tailored according to the specific medical history of a patient. For example, an expected pharmacodynamic model can be constructed based on previous data collected from the patient. Other methods for selecting an expected pharmacodynamic model are also contemplated such as, for example, using individual patient genetic factors that impact drug metabolism.

Figure 4:
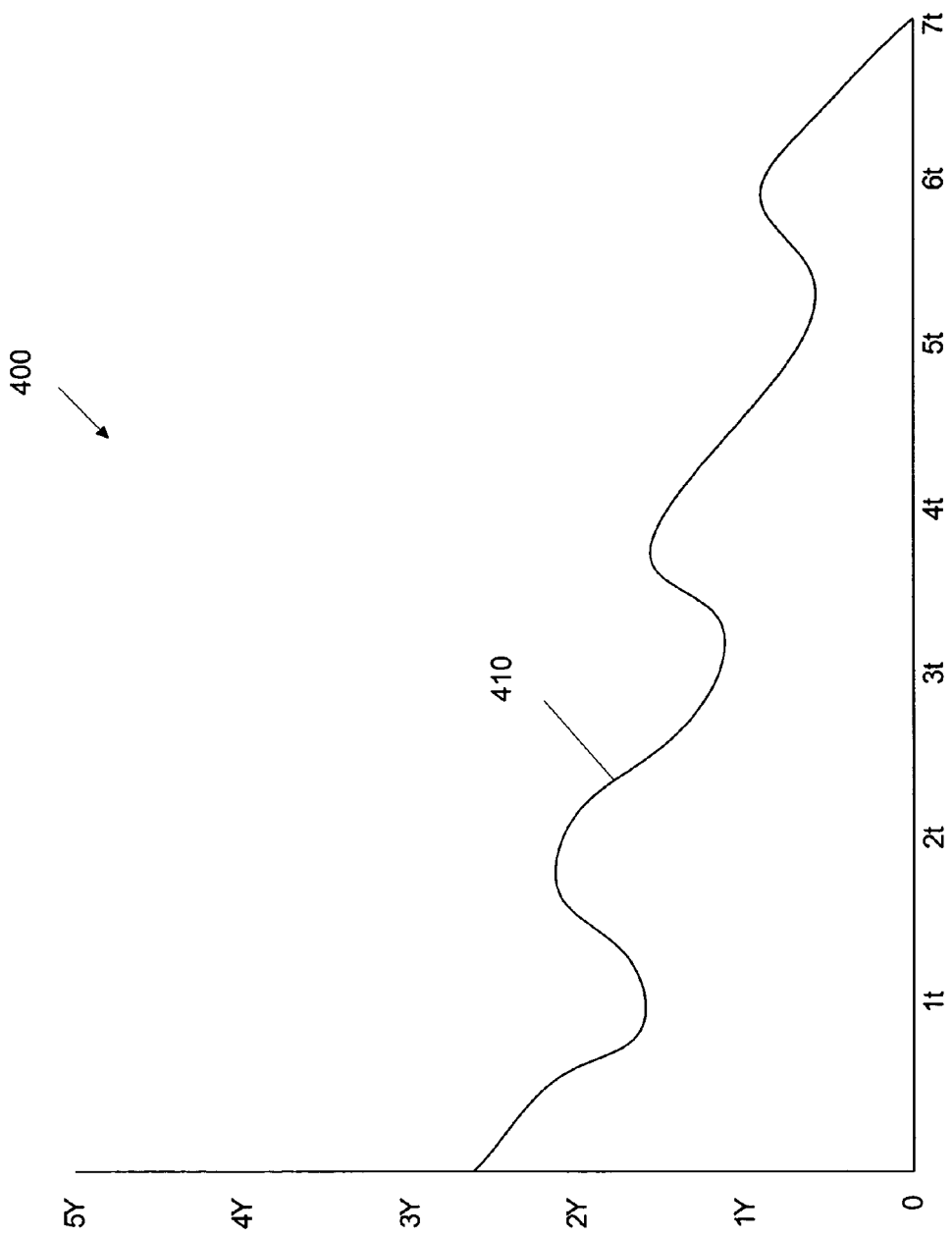
FIG. 4 illustrates an example expected pharmacodynamic model.
Figure 5:
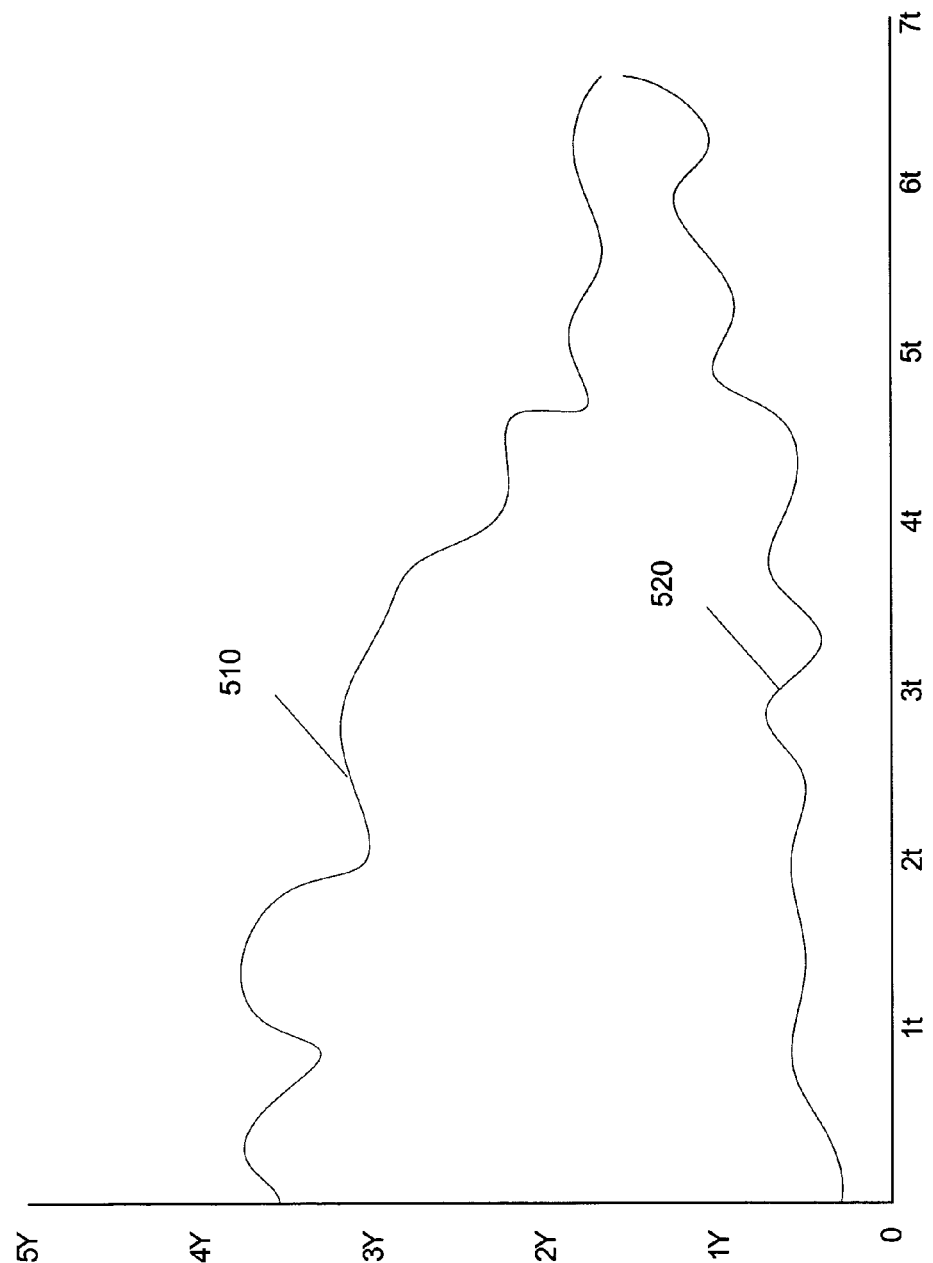
FIG. 5 illustrates another example expected pharmacodynamic model.

Examples of expected pharmacodynamic models are illustrated in FIGS. 4 and 5. The model 400 shown in FIG. 4 illustrates a pharmacological effect 410 that generally decreases over time. As note above, the slope and initial conditions of the effect 410 can be chosen based on population or individual patient factors.

For example, model 400 can be an expected pharmacological effect for a patient's systolic blood pressure. A patient's systolic blood pressure typically decreases within a few hours after an ACE inhibitor is taken. Model 400 can be used as an expected pharmacodynamic model of how the patient's systolic blood pressure should react over time based on ingestion of the ACE inhibitor.

Another example model 500 illustrated in FIG. 5 involves two expected pharmacological effects 510 and 520. For example, the administration of some heart drugs can result in multiple pharmacological effects such as, for example, variations in heart rate and heart rate variability over time. For example, assuming dosages of medication at times 1t and 3t, model 500 illustrates a decrease in heart rate (pharmacological effect 510) and an increase in heart rate variability (pharmacological effect 520) over time. By collecting data related to heart rate using a sensor such as an implanted or non-implanted device, data associated with the pharmacological effects of a drug on a patient can be compared to the expected pharmacodynamic model 500 illustrated in FIG. 5.

Referring back to FIG. 3, once the data collected from the patient is compared to the expected pharmacodynamic model in operation 320, control is then passed to operation 330 and a determination is made as to whether the collected data corresponds to the expected pharmacodynamic model. In one embodiment, the comparison is made by computing deviations between the models. In another embodiment parameters of the expected model (e.g., time of the step-wise change, delta increment) are computed in advance and stored in the system.

If the collected data corresponds to the expected pharmacodynamic model, control is passed back to operation 310 and collection of data continues. If the collected data does not correspond to the expected pharmacodynamic model, control is passed to operation 340, and specific steps such as reporting, alarming, or automatic modifications to drug therapy can occur.

For example, depending on the type and magnitude of deviation of the collected data from the expected pharmacodynamic model, various reports and alarms can be generated. In one embodiment, if the collected data indicates an adverse side effect to a given drug, a side-effect report is generated that is then forwarded to the caregiver and/or patient. In another embodiment, if the collected data indicates a resistance to a drug, a resistance report is generated that is then forwarded to the caregiver and/or patient. In yet another embodiment, if the collected data indicates non-compliance with a drug regimen, a non-compliance report is generated that is then forwarded to the caregiver and/or patient.

If the nature of the deviation from the expected pharmacodynamic model is such that immediate action is desirable, alarms can be sent to the caregiver and/or to the patient to alert of the potential problem.

In another embodiment, the system can react to a deviation from the expected pharmacodynamic model by automatically modifying the patient's drug therapy regimen. For example, if the drug dispenser is an implanted drug pump, the system can modify drug therapy provided by the pump (e.g., increase or decrease frequency and/or amount) based on the comparison of the measured data to the expected pharmacodynamic model.

More than one device can also be used to measure multiple aspects of the patient's pharmacological effect. For example, multiple devices (or a single device with multiple capabilities) can be used to collect data related to multiple different pharmacological effects such as, for example and without limitation, a patient's heart rate and blood pressure.

Further, in some embodiments, multiple expected pharmacodynamic models can be compared to data collected with respect to the pharmacological effect of multiple drugs on a patient. Or, alternatively, a single expected pharmacodynamic model can be used that accounts for the interaction of the pharmacological effect of multiple drugs.

In addition, in some embodiments, not all of the collected data is forwarded to the host 112 for processing. For example, in some embodiments, the device 102 and/or the ITU 108 can conduct at least initial processing of the collected data to identify, for example, data that would indicate that immediate intervention is necessary.

Various advantages are associated with the use of systems configured in a manner similar to example systems 100 and 200 described above. For example, the collected data can be used monitor drug effects, side-effects, patient compliance, and time of intake. In addition, the data can be used to assist in the identification of comorbidities and drug interactions.

Further, the collected data can be used to identify beneficial dosage and/or therapy modifications such as, for example and without limitation, reevaluation of therapy if resistance is identified, or a decrease in drug amount if an adverse side effect is identified.

II. Advanced Patient Management System

In some embodiments, the systems 100 and 200 described above are implemented as part of an advanced patient management ("APM") system configured to collect patient-specific information, store and collate the information, and generate actionable recommendations to enable the predictive management of patients.

Embodiments of the APM system can be configured to monitor patient compliance with a drug regimen, determine and monitor efficacy of the drug regimen, and monitor any side effects resulting from the drug regimen. The APM system can be configured to use drug parameters and patient health history provided by at least one of a primary care giver (e.g., a doctor), a drug network and a drug information database in conjunction with patient physical indicators to help determine accuracy of the drug regimen compliance, drug efficacy, and side effects. The example APM systems disclosed herein can also be configured to produce reports related to compliance, efficacy, and side effects of the drug regimen and communicate those reports to various destinations, such as, for example, a primary caregiver, the patient, a pharmacokinetics database, or a drug network.

Figure 6:
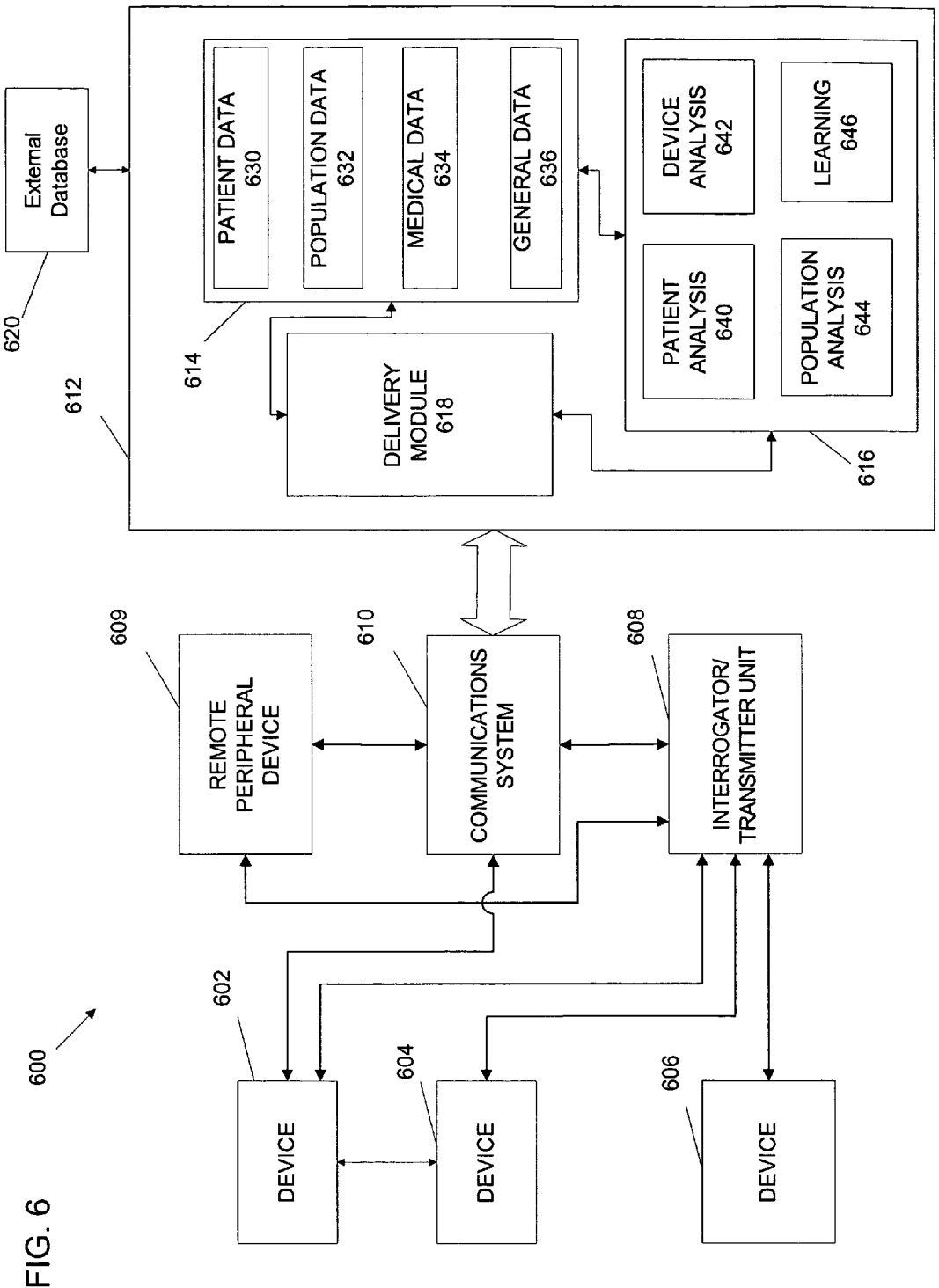
FIG. 6 illustrates an example advanced patient management system made in accordance with the present invention.

FIG. 6 illustrates an example APM system 600 made in accordance with the present invention. APM system 600 generally includes the following components: devices 602, 604, and 606, an interrogator/transceiver units 608, a communication system 610, a remote peripheral device 609, and a host 612.

Each component of the APM system 600 can communicate using the communication system 610. Some components can also communicate directly with one another. For example, devices 602 and 604 can be configured to communicate directly with one another. The various components of the example APM system 600 illustrated herein are described below.

a. Devices

Devices 602, 604, and 606 can be implantable devices or external devices that can provide at least one of the following functions with respect to a patient in addition to other possible functions: (1) sensing/measuring, (2) data analysis, (3) therapy, (4) distribution of product, and (5) communication. For example, in one embodiment, devices 602, 604, and 606 are either implanted or external devices used to sense or measure a variety of physiological, subjective, and environmental conditions of a patient using electrical, mechanical, and/or chemical means. The devices 602, 604, and 606 can be configured to automatically gather data or can require manual intervention by the patient. The devices 602, 604, and 606 can be devices that are positioned external and separated from the patient, positioned on an external surface of the patient, or positioned within the patient as an implanted device or sensor. The devices 602, 604, and 606 can be configured to store data related to the physiological and/or subjective measurements and/or transmit the data to the communication system 610 using a variety of methods, described in detail below. Although three devices 602, 604, and 606 are illustrated in the example embodiment shown, more or fewer devices can be used for a given patient.

The devices 602, 604, and 606 can be configured to analyze the measured data and act upon the analyzed data. For example, the devices 602, 604, and 606 are configured to modify therapy or provide alarm indications based on the analysis of the data.

In one embodiment, devices 602, 604, and 606 also provide therapy. Therapy can be provided automatically or in response to an external communication. Devices 602, 604, and 606 are programmable in that the characteristics of their sensing, therapy (e.g., duration and interval), or communication can be altered by communication between the devices 602, 604, and 606 and other components of the APM system 600. Devices 602, 604, and 606 can also perform self-checks or be interrogated by the communication system 610 to verify that the devices are functioning properly.

In another embodiment, devices 602, 604, and 606 also provide disbursement of product (such as drug dispensers 222 and 902). Product disbursement can be provided automatically or in response to an external communication. Some example products that can be dispersed include pills/drugs that are part of a patient drug regimen and testing/sampling products for patient conducted tests or sampling bodily products.

The devices 602, 604, and 606 can be configured to communicate with the patient and with other devices and features of the APM. For example, the devices 602, 604, and 606 can communicate with a patient using sound or visual prompts to, for example, obtain answers to questions, remind the patient to perform certain tasks, and warn the patient about the presence of predetermined threshold trends and conditions that represent the patient's well-being. The devices 602, 604, and 606 can also include user interface features such as a keypad, touch control screen, or other input device that facilitate communication between the patient and the devices 602, 604, and 606. Additional examples of different embodiments of the devices 602, 604, and 606 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

Derived measurements can also be determined from the implantable device sensors. Examples of such derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 602, 604, and 606 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)). The physiologic signals collected by external sensors could be uniquely associated with the patient by verifying device ID via a telemetry link.

Devices 602, 604, and 606 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 602, 604, and 606 (for example, device 606) can be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 606 can be any device that accepts input from a patient or other concerned individual and/or provides information in a format that is recognizable to the patient.

The APM system 600 can also include one or more remote peripheral devices 609. The remote peripheral device 609 can include, for example and without limitation, cellular telephones, pagers, PDA devices, facsimiles, remote computers, printers, video and/or audio devices, etc. The remote peripheral device 609 can communicate using wired or wireless technologies and can be used by the patient or caregiver to communicate with the communication system 610 and/or the host 612. For example, the remote peripheral device 609 can be used by the caregiver to receive alerts from the host 612 based on data collected from the patient and to send instructions from the caregiver to either the patient or other clinical staff. In another example, the remote peripheral device 609 is used by the patient to receive periodic or real time updates and alerts regarding the patient's health and well-being.

b. Interrogator/Transceiver Unit

Figure 7:
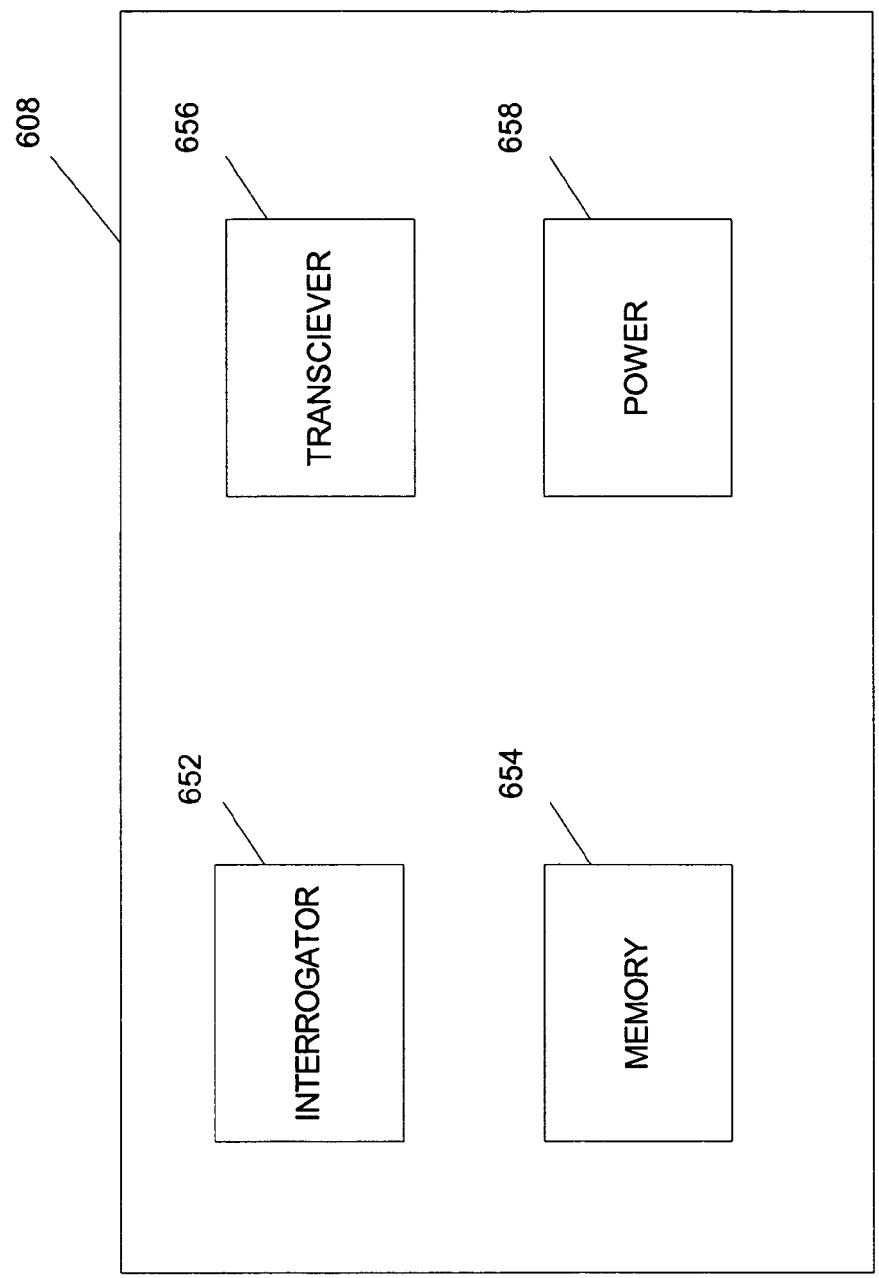
FIG. 7 illustrates an example interrogator/transceiver unit made in accordance with the present invention.

Referring now to FIG. 7, the example APM system 600 includes one or more interrogator/transceiver units ("ITUs"), such as ITU 608. In illustrated embodiments, the ITU is configured in a manner similar to that disclosed in U.S. patent application Ser. No. 10/330,677, filed Dec. 27, 2002, and entitled "Advanced Patient Management System Including Interrogator/Transceiver Unit," which is hereby incorporated by reference in its entirety.

The ITU 608 can include an interrogator module 652 for sending and receiving data from a device, such as devices 602, 604, and 606, a memory module 654 for storing data, and a transceiver module 656 for sending and receiving data to and from other components of the APM system 600. The transceiver module can also operate as an interrogator of the devices 602, 604 and 606. The ITU 608 also includes a power module 658 that provides power.

The ITU 608 can perform one or more of the following functions: (1) data storage; (2) data analysis; (3) data forwarding; (4) patient interaction; (5) patient feedback; and (6) data communications. For example, the ITU 608 can facilitate communications between the devices 602, 604, and 606 and the communication system 610. The ITU 608 can, periodically or in real-time, interrogate and download into memory clinically relevant patient data from the devices 602, 604, and/or 606. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, physiological conditions that represent efficacy and compliance of a drug regimen, and any other clinical information necessary to ensure patient health and proper device function. The data is sent to the ITU 608 by the devices 602, 604, and 606 in real-time or periodically uploaded from buffers in the devices.

The ITU 608 can also allow patient interaction. For example, the ITU 608 can include a patient interface and allow the patient to input subjective data. In addition, the ITU 608 can provide feedback to the patient based on the data that has been analyzed or based on information communicated by the communication system 610.

In another embodiment, the ITU 608 includes a telemetry link from the devices to a network that forms the basis of a wireless LAN in the patient's home. The ITU 608 systematically uploads information from the devices 602, 604, and/or 606 while the patient is sleeping, for example. The uploaded data is transmitted through the communication system 610 or directly to the host 612. In addition, in one embodiment the ITU 608 functions in a hybrid form, utilizing wireless communication when available and defaulting to a local wireless portal or a wired connection when the wireless communication becomes unavailable.

When the interrogator 652 uses radio frequency to communicate with the devices 602, 604, 606, the ITU 608 can be in the form of a small device that is placed in an inconspicuous place within the patient's residence. Alternatively, the ITU 608 can be implemented as part of a commonly used appliance in the patient's residence. For example, the ITU can be integrated with an alarm clock that is positioned near the patient's bed. In another embodiment, the ITU can be implemented as part of the patient's personal computer system. Other embodiments are also possible.

In another embodiment, the ITU 608 can comprise a hand-held device such as a PDA, cellular telephone, or other similar device that is in wireless communication with the devices 602, 604, and 606. The hand-held device can upload the data to the communication system 610 wirelessly. Alternatively, the hand-held device can periodically be placed in a cradle or other similar device that is configured to transmit the data to the communication system 610.

If multiple devices, such as devices 602, 604, and 606, are provided for a given patient, each device can include its own means for communicating with the ITU 608 or communication system 610. Alternatively, a single telemetry system can be implemented as part of one of the devices, or separate from the devices, and each device 602, 604, and 606 can use this single telemetry system to communication with the ITU 608 or the communication system 610.

In yet another embodiment, the devices 602, 604, and 606 include wires or leads extending from devices 602, 604, and 606 to an area external of the patient to provide a direct physical connection. The external leads can be connected, for example, to the ITU 608 or a similar device to provide communications between the devices 602, 604, and 606 and the other components of the APM system 600.

The APM system 600 can also involve a hybrid use of the ITU 608. For example, the devices 602, 604, and 606 can intelligently communicate via short-range telemetry with the ITU when the patient is located within the patient's home and communicate directly with the communication system 610 or host 612 when the patient is traveling. This can be advantageous, for example, to conserve battery power when the devices are located near an ITU.

c. Communication System

Figure 8:
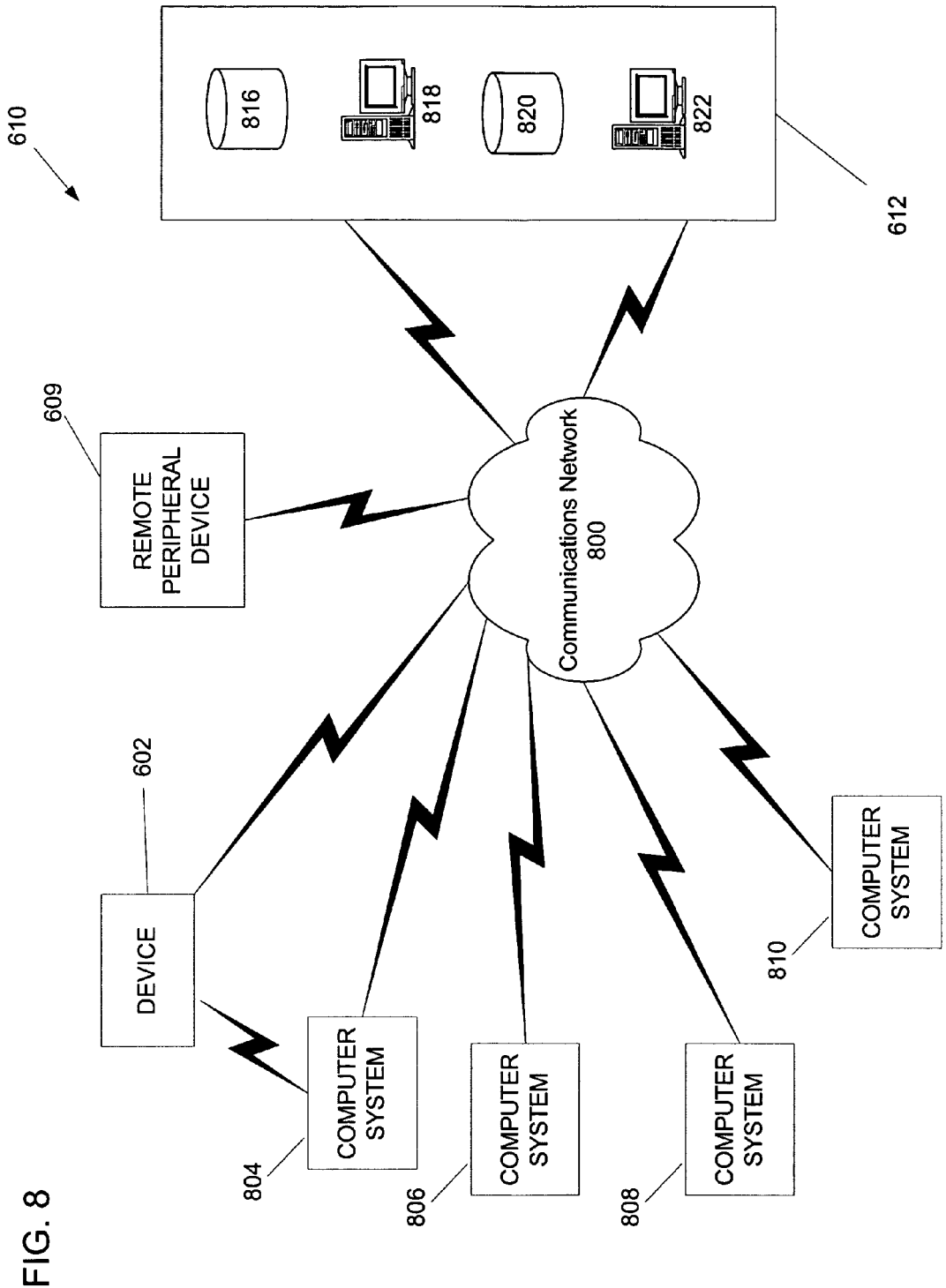
FIG. 8 illustrates an example communication system made in accordance with the present invention.

Communication system 610 provides for communications between and among the various components of the APM system 600, such as the devices 602, 604, and 606, host 612, and remote peripheral device 609. FIG. 8 illustrates one embodiment for the communication system 610 made in accordance with the present invention. The communication system 610 includes a plurality of computer systems 804, 806, 808, and 810, as well as device 602, host 612, and remote peripheral device 609, connected to one another by a communication network 800. The communication network 800 can be, for example, a local area network (LAN), wide area network (WAN), or the Internet. Communications among the various components, as described more fully below, can be implemented using wired or wireless technologies.

In the example embodiment illustrated, the host 612 includes server computers 818 and 822 that communicate with computers 804, 806, 808, and 810 using a variety of communications protocols that are described more fully below. The server computers 818 and 822 store information in databases 816 and 820. This information can also be stored in a distributed manner across one or more additional servers.

A variety of communication methods and protocols can be used to facilitate communication between devices 602, 604, and 606, ITU 608, communication system 610, host 612, and remote peripheral device 609. For example, wired and wireless communications methods can be used. Wired communication methods can include, for example and without limitation, traditional copper-line communications such as DSL, broadband technologies such as ISDN and cable modems, and fiber optics, while wireless communications can include cellular, satellite, radio frequency (RF), Infrared, etc.

d. Host

Referring again to FIG. 6, the example host 612 includes a database module 614, an analysis module 616, and a delivery module 618. Host 612 preferably includes enough processing power to analyze and process large amounts of data collected from each patient, as well as to process statistics and perform analysis for large populations. For example, the host 612 can include a mainframe computer or multi-processor workstation. The host 612 can also include one or more personal computer systems containing sufficient computing power and memory. The host 612 can include storage medium (e.g., hard disks, optical data storage devices, etc.) sufficient to store the massive amount of high-resolution data that is collected from the patients and analyzed.

The host 612 can also include identification and contact information (e.g., IP addresses, telephone numbers, or a product serial number) for the various devices communicating with it, such as ITU 608 and peripheral device 609. For example, each ITU 608 is assigned a hard-coded or static identifier (e.g., IP address, telephone number, etc.), which allows the host 612 to identify which patient's information the host 612 is receiving at a given instant. Alternatively, each device 602, 604, and 606 can be assigned a unique identification number, or a unique patient identification number can be transmitted with each transmission of patient data.

Referring again to FIG. 6, the example database module 614 includes a patient database 630, a population database 632, a medical database 634, and a general database 636, all of which are described further below.

The patient database 630 includes patient specific data, including data acquired by the devices 602, 604, and 606. The patient database 630 also includes a patient's medical records, the patient's current health information, targeted health information, and drug information. The patient database 630 can include pharmacogenomic information describing individual genetic differences that could impact drug metabolism. The patient database 630 can include historical information regarding the devices 602, 604, and 606. For example, if device 602 is an implantable cardioverter defibrillator (ICD), the patient database 630 records the following device information: P and R measurements, pacing frequency, pacing thresholds, shocking events, recharge time, lead impedance, battery voltage/remaining life, ATR episode and EGMs, histogram information, and other device-specific information. The information stored in the database 630 can be recorded at various times depending on the patient requirements or device requirements. For example, the database 630 is updated at periodic intervals that coincide with the patient downloading data from the device. Alternatively, data in the database 630 can be updated in real time. Typically, the sampling frequency depends on the health condition being monitored and the co-morbidities.

The population database 632 includes non-patient specific data, such as data relating to other patients and population trends. The population database 632 also records epidemic-class device statistics and patient statistics. The population database 632 also includes data relating to staffing by health care providers, environmental data, drugs, etc. In some cases, patient information from the patient database 630 can be added to the population database to supplement and maintain currency of the population database information and trends.

The example medical database 634 includes clinical data relating to the treatment of diseases. For example, the medical database 634 includes historical trend data for multiple patients in the form of a record of progression of their disease(s) along with markers of key events. The medical database could also include clinical study results.

The general database 636 includes non-medical data of interest to the patient. The general database 636 can include information relating to, for example, news, finances, shopping, technology, entertainment, and/or sports. The general database 636 can be customized to provide general information of specific interest to the patient. For example, stock information can be presented along with the latest health information as detected from the devices 602, 604, and 606.

In another embodiment, information is also provided from an external source, such as external database 600. For example, the external database 600 can include external medical records and drug prescription records maintained by a pharmacy for a patient, as well as pharmacokinetics, pharmacodynamics, drug side effects, drug compatibility, and other drug related information for the type of drugs that have been prescribed for a patient.

The example analysis module 616 includes a patient analysis module 640, device analysis module 642, population analysis module 644, and learning module 646. Patient analysis module 640 can utilize information collected by the APM system 600, as well as information from other relevant sources, to analyze data related to a patient and provide timely and predictive assessments of the patient's well-being. In performing this analysis, the patient device module 640 can utilize data collected from a variety of sources, include patient specific physiological and subjective data collected by the APM system 600, medical and historical records (e.g., lab test results, histories of illnesses, etc., drugs currently and previously administered, etc.), as well as information related to population trends provided from sources external to the APM system 600.

For example, in one embodiment, the patient analysis module 640 makes a predictive diagnosis of an oncoming event based on information stored in the database module 614. For example, the data continuously gathered from a device of a given patient at a heightened risk for a chronic disease event (such as de-compensations in heart failure) is analyzed. Based on this analysis, therapy, typically device-based or drug, can then be applied to the patient either through the device or through clinician intervention.

In another example embodiment, the patient analysis module 640 provides a diagnosis of patient health status and predicted trend based on present and recent historical data collected from a device as interpreted by a system of expert knowledge derived from working practices within clinics. For example, the patient analysis module 640 performs probabilistic calculations using currently-collected information combined with regularly-collected historical information to predict patient health degradation.

In another example embodiment, the patient analysis module 640 can conduct pre-evaluation of the incoming data stream combined with patient historical information and information from patients with similar disease states. The pre-evaluation system is based on data derived from working clinical practices and the records of outcomes. The derived data is processed in an expert system (i.e., neural network, fuzzy logic system, or equivalent system) to reflect the clinical practice. Further, the patient analysis module 640 can also provide means for periodic processing of present and historical data to yield a multidimensional health state indication along with disease trend prediction, next phase of disease progression co-morbidities, and inferences about what other possible diseases can be involved. The patient analysis module 640 can also integrate data collected from internal and external devices with subjective data to optimize management of overall patient health.

Device analysis module 642 analyzes data from the devices 602, 604, and 606 and ITU 608 to predict and determine device issues or failures. For example, if an implanted device 602 fails to communicate at an expected time, device analysis module 642 determines the source of the failure and takes action to restore the performance of the device 602. The device analysis module 642 can also perform additional deterministic and probabilistic calculations. For example, the device analysis module 642 gathers data related to charge levels within a given device, such as an ICD, and provides analysis and alerting functions based on this information if, for example, the charge level reaches a point at which replacement of the device and/or battery is necessary. Similarly, early degradation or imminent failure of implanted devices or leads can be identified and proactively addressed, or at-risk devices can be closely monitored.

Population analysis module 644 uses the data collected in the database module 614 to manage the health of a population. For example, a clinic managing cardiac patients can access the APM system 600 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment, population analysis module 644 trends the patient population therapy and management as recorded by the devices and directs health care resources to best satisfy the needs of the population. The resources can include people, facilities, supplies, and/or drugs. In other embodiments, the population analysis module detects epidemics and other events that affect large population groups. The population analysis module 644 can issue alerts that can initiate a population quarantine, redirect resources to balance size of staffing with number of presenting population, and predict future need of qualified specialists.

The population analysis module 644 can utilize a variety of characteristics to identify like-situated patients, such as, for example, sex, age, genetic makeup, etc. The population analysis module 644 can develop large amounts of data related to a given population based on the information collected by the APM system 600. In addition, the population analysis module 644 can integrate information from a variety of other sources. For example, the population analysis module 644 can utilize data from public domain databases (e.g., the National Institute of Health), public and governmental and health agency databases, private insurance companies, medical societies (e.g., the American Heart Association), and genomic records (e.g., DNA sequences).

In one embodiment of the invention, the host 612 can be used as a "data clearinghouse," to gather and integrate data collected from the devices 602, 604, and 606, as well as data from sources outside the APM system 600, such as the external database 600. The integrated data can be shared with other interested entities, subject to privacy restrictions, thereby increasing the quality and integration of data available.

Learning module 646 analyzes the data provided from the various information sources, including the data collected by the advanced patient system 600 and external information sources. For example, the learning module 646 analyzes historical symptoms, diagnoses, and outcomes along with time development of the diseases and co-morbidities. The learning module 646 can be implemented via an expert system.

The learning module 646 can be partially trained (i.e., the learning module 646 can be implemented with a given set of inference rules and then learn as the APM system functions) or untrained (i.e., the learning module 646 is initiated with no preset values and must learn from scratch as the APM system functions). In other alternative embodiments, the learning module 646 can continue to learn and adjust as the APM system functions (i.e., in real time), or the learning module 646 can remain at a given level of learning and only advanced to a higher level of understanding when manually allowed to do so.

In an expert system embodiment, new clinical information is presented to create new neural network coefficients that are distributed as an expert system knowledge upgrade. The learning module 646 can include a module for verifying the expert system conclusions for clinical accuracy and significance. The learning module can analyze a database of test cases, appropriate outcomes and relative occurrence of misidentification of the proper outcomes. In some embodiments, the learning module 646 can update the analysis module 616 when the analysis algorithms exceed a threshold level of acceptable misidentifications.

The example learning module 646 uses various algorithms and mathematical modeling such as, for example, trend and statistical analysis, data mining, pattern recognition, cluster analysis, neural networks and fuzzy logic. Learning module 646 can perform deterministic and probabilistic calculations. Deterministic calculations include algorithms for which a clear correlation is known between the data analyzed and a given outcome. For example, there can be a clear correlation between the energy left in a battery of an implantable device and the amount of time left before the battery must be replaced.

A probabilistic calculation involves the correlation between data and a given outcome that is less than 100 percent certain. Probabilistic determinations require an analysis of several possible outcomes and an assignment of probabilities for those outcomes (e.g., an increase in weight of a patient can, at a 25 percent probability, signal an impending decompensation event and/or indicate that other tests are needed). The learning module 646 performs probabilistic calculations and selects a given response based on a highest probability. In doing so the module could use prior probability of an event derived from population or clinical study database. Further, as the learning module 646 "learns" for previous determinations (e.g., through a neural network configuration), the learning module 646 becomes more proficient at assigning probabilities for a given data pattern, thereby being able to more confidently select a given response. As the amount of data that has been analyzed by the learning module 646 grows, the learning module 646 becomes more and more accurate at assigning probabilities based on data patterns. A bifurcated analysis can be performed for diseases exhibiting similar symptoms. As progressive quantities of data are collected and the understanding of a given disease state advances, disease analysis is refined where a former singular classification can split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 646 is capable of tracking and forecasting a patient's clinical status with increasing levels of sophistication by measuring a number of interacting co-morbidities, all of which can serve individually or collectively to degrade the patient's health. This enables learning module 646, as well as caregivers, to formulate a predictive medical response to oncoming acute events in the treatment of patients with chronic diseases such as heart failure, diabetes, renal dysfunction, cancer, and asthma/COPD, as well as possibly head-off acute catastrophic conditions such as MI and stroke.

Delivery module 618 coordinates the delivery of feedback based on the analysis performed by the host 612. In response to the analysis module 616, delivery module 618 can manage the devices 602, 604, and 606, perform diagnostic data recovery, program the devices, and otherwise deliver information as needed. In some embodiments, the delivery module 618 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif., or Guidant patient personal web page provided by Guidant Corporation of Indianapolis, Ind. For example, a patient can access his or her My Yahoo homepage or Guidant patient personal web page and receive information regarding current health and trends derived from the information gathered from the devices 602, 604, and 606, as well as other health information gathered from other sources. The patient can also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 600, as well as any analysis performed by the system 600, is delivered by delivery module 618 to a caregiver's hospital computer system for access by the caregiver. A standard or custom interface facilitates communication between the APM system 600 and a legacy hospital system used by the caregiver so that the caregiver can access all relevant information using a system familiar to the caregiver.

The APM system 600 can also be configured so that various components of the system (e.g., ITU 608, communication system 610, and/or host 612) provide reporting to various individuals (e.g., patient and/or caregiver). For example, different levels of reporting can be provided by (1) the ITU 608 and (2) the host 612. The ITU 608 can be configured to conduct rudimentary analysis of data gathered from devices 602, 604, and 606, and provide reporting should an acute situation be identified. For example, if the ITU 608 detects that a significant heart arrhythmia is imminent or currently taking place, the ITU 608 provides reporting to the patient in the form of an audible or visual alarm.

The host 612 can provide a more sophisticated reporting system. For example, the host 612 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the APM system 600, the delivery module 618 can communicate directly with the devices 602, 604, and 606, contact a pharmacy to order a specific drug for the patient, and/or contact 911 emergency response. In an alternative embodiment, the delivery module 618 and/or the patient can also establish a voice communication link between the patient and a caregiver, if warranted.

In addition to forms of reporting including visual and/or audible information, the APM system 600 can also communicate with and reconfigure one or more of the devices 602, 604, and 606. For example, if device 602 is part of a cardiac rhythm management system, the host 612 can communicate with the device 602 and reconfigure the therapy provided by the cardiac rhythm management system based on the data collected from one or more of the devices 602, 604, and 606. In another embodiment, the delivery module 618 can provide to the ITU 608 recorded data, an ideal range for the data, a conclusion based on the recorded data, and a recommended course of action. This information can be displayed on the ITU 608 for the patient to review or made available on the peripheral device 609 for the patient and/or clinician to review.

Figure 9:
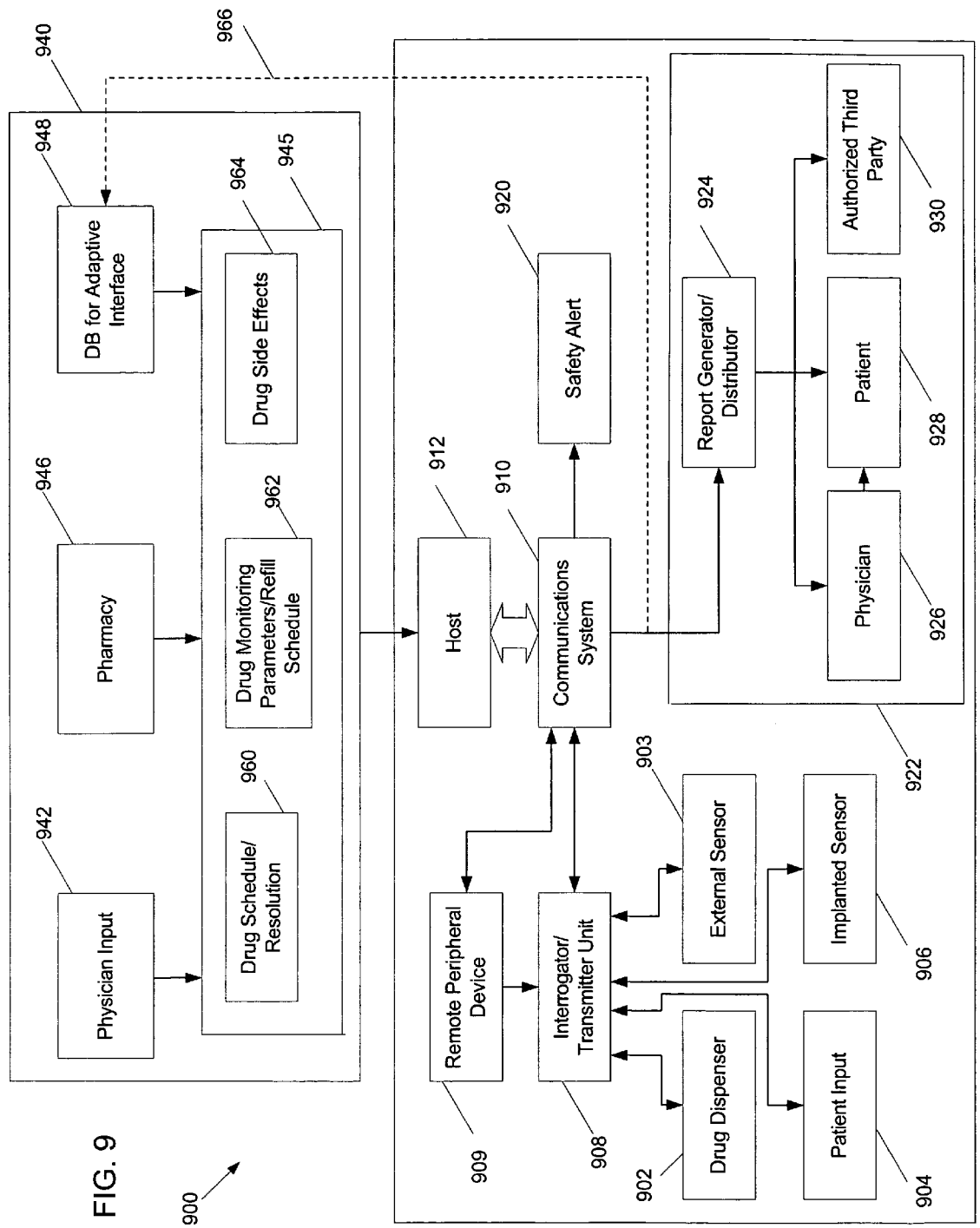
FIG. 9 illustrates another example advanced patient management system made in accordance with the present invention.

III. System Including Integrated Drug Dispensing and Patient Management Monitoring Referring now to FIG. 9, an example system 900 is shown. In illustrated embodiments, system 900 is configured in a manner similar to that disclosed in U.S. patent application Ser. No. 10/970,286, filed on even date herewith, and entitled "Integrated Drug Dispensing and Patient Management Monitoring," the entirety of which is hereby incorporated by reference.

System 900 generally includes the following components: devices 902, 904, 906, and 908, interrogator/transceiver unit 908, communication system 910, a remote peripheral device 909, and a host 912. APM system 900 also includes a safety alert 920, a report device 922 that includes a report generator/distributor 924 and reports to a physician 926, a patient 928, and an authorized third party 930. An external database 940 of APM system 900 includes a physician input 942, a pharmacy interface 946, and a pharmacology database for adaptive interface 948 that provide drug parameters 945 in the form of, for example, a drug schedule/resolution 960, drug monitoring parameters/refill schedule 962 and drug side effects 964. An automated feedback 966 of APM system 900 can be used to communicate information via the communications system 910 back to the interface 948. Other feedback loops (for example, see the method of FIG. 10) can be used to communicate real-time or periodic patient information back to various databases and other features associated with APM system 900.

Each component of the APM system 900 can communicate using the communication system 910, or can be configured to communicate directly with one another. The APM system 900 can be used to collect certain drug and patient information and provide reports to various parties related to the patient's well-being, compliance with a drug regimen, side effects of the drug regimen, physical indicators of the drug efficacy, and information about the drug supply and other relevant information related to the patient.

APM system 900 can be useful in the following scenario. Following diagnosis of a disease, the physician of a patient prescribes a drug or a set of drugs to treat the disease. When the prescription gets filled by a major drug network, the specific drug parameters 945 (e.g., schedule of drug administration, resolution of data, pharmacokinetics, side effects, expected results, compatibility with other drugs, etc.) are uploaded to the host 912 either directly or via the communication system 910 from the drug network 946, the physician 942, and the drug database 944. The APM system 900 then provides patient display updates and prompts based on the merged inputs from the external database 940 via the interrogator/transmitter unit 908 and the devices 902, 903, 904, 906 and 909.

In the illustrated embodiment, device 902 is a drug dispenser that can be used to dispense drugs/pills directly to the patient in their home based on the prescription information. In some embodiments, the drug dispenser 902 is configured in a manner similar to that described in U.S. patent application Ser. No. 10/787,045, filed on Feb. 25, 2004, and entitled "Advanced Patient and Medication Therapy Management System and Method," which is hereby incorporated by reference in its entirety.

The APM system 900 records the patient prompts and dispensed drugs, and generates various reports via the reporting device 922 based on the inputs from the patient via the devices 902, 903, 904, 906 and 909, and inputs from the external database 940. The generated reports can be sent to, for example, the physician 926, back to the patient 928, or to an authorized third party 930. The reports and other information gathered by the devices 902, 903, 904, 906 and 909 as well as information initially provided by database 940 can be communicated back to the database 940 or to the host 912 to perform updates to the databases and to perform analysis and statistics of the information for the patient and the population. In some embodiments, the reports can be generated or initiated by the host and the reporting device 922 can be used only to distribute the reports via the communication system 910. The available information and reports can also be used to update the patient's health history kept by the physician, update the drug database, update the drug network, or create trends for future drug treatments, therapy and other forms of patient care, for example, so that the patient is not prescribed a drug, combination of drugs, or particular drug dosage again in the future due to certain undesired side effects.

The database for adaptive interface 948 can use some of the available information in real-time or periodic intervals to issue an alert or automatically update and/or change the patient therapy or drug treatment regimen. For example if patient experiences heavy atrial fibrillation an anticoagulant could be introduced to prevent a risk of stroke. Information and reports provided to the physician can be used by professionals at a clinic or by the physician directly to override the current drug prescription by changing dosages, time intervals, or to change drug or drugs being taken by the patient.

APM system 900 can be particularly useful for monitoring a patient during application of a new or revised drug regimen because system 900 can identify certain problems and complications relatively quickly and can likewise monitor sensor feedback and patient performance in a reliable, time-sensitive manner for an indication that the drug regimen is working properly. APM system 900 is also configured to perform certain functions automatically while providing for relative ease in modifying system parameters, for example, a drug prescription, patient condition thresholds for alarm indicators, etc.

Figure 10:
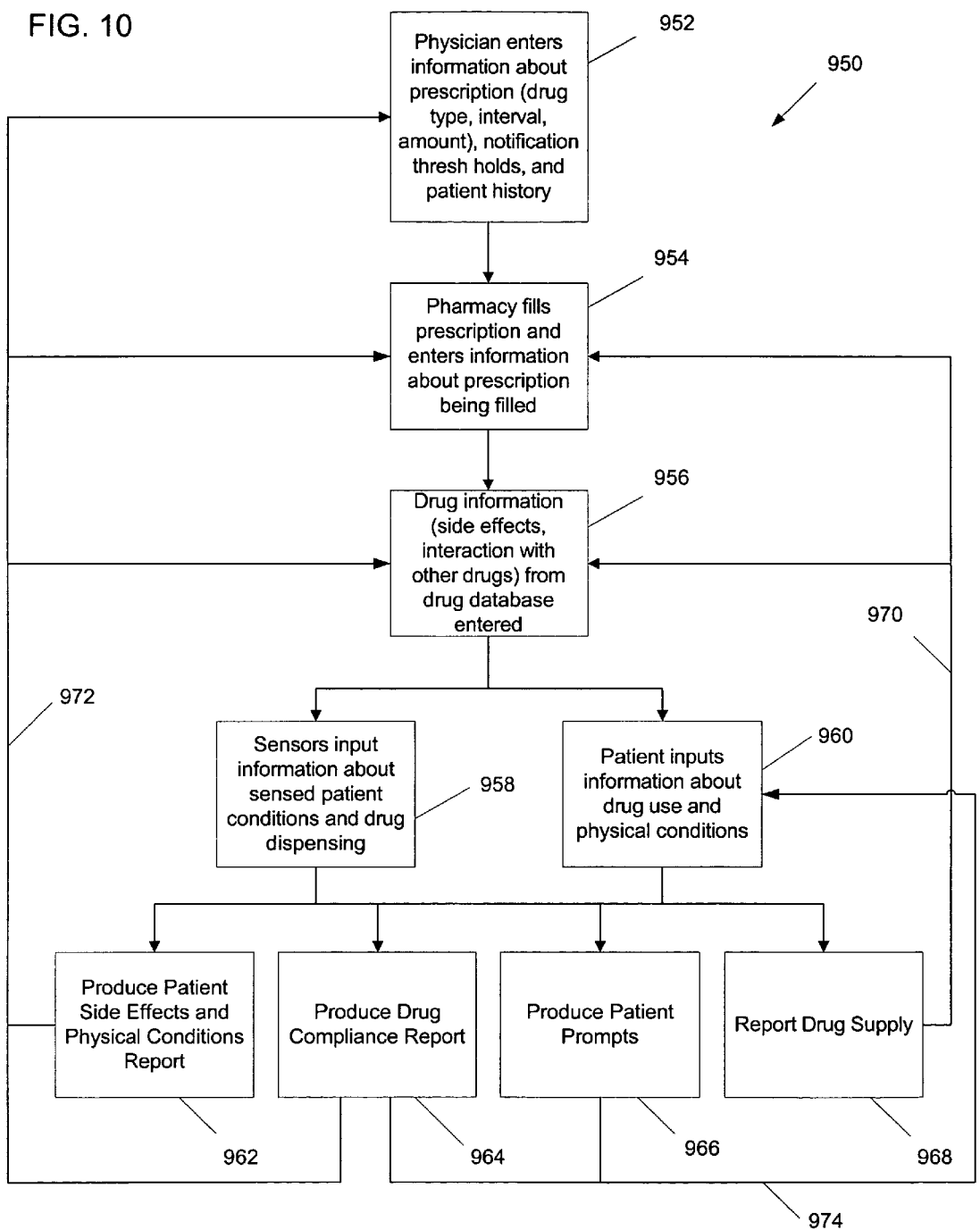
FIG. 10 illustrates an example method for monitoring patient compliance with and efficacy of a patient drug regimen.

A method 950 of using an APM system according to principles of the present invention to monitor and implement a drug regimen and provide reports of patient conditions and drug regimen compliance is illustrated with reference to FIG. 10. The method includes a step 952 of the physician entering information about the prescription (e.g., drug type, interval, and amount), notification thresholds, and the patient health history into the APM system. Another step 954 includes the pharmacy filling the prescription and entering information about the prescription being filled into the APM system. A further step 956 includes downloading drug information (e.g., side effects and interaction with other drugs) from a pharmacology database into the APM system. At the patient side of the method, a step 958 includes the sensors inputting information about sensed patient conditions and drug dispensing into the APM system, and the patient inputting information about drug use and physical conditions into the APM system.

The method 950 also includes producing a number of reports in response to the information gathered into the APM system in steps 952, 954, 956, 958 and 960. A step 962 includes producing a patient side effects and physical conditions report, a step 964 includes producing a drug compliance report, a step 966 includes producing patient prompts, and a step 968 includes reporting drug supply information. The reports 962, 964, 966 and 968 and other relevant patient and drug information can be fed back to any of the other steps in the method as shown by feedback loops 970, 972, 974.

IV. Conclusion

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules can be implemented in software, in firmware, in special purpose digital logic, analog circuits, and any combination thereof without deviating from the spirit and scope of the present invention as recited within the claims attached hereto.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A patient management system for monitoring a patient, the system comprising:
   an implantable device configured to measure data associated with at least one pharmacological effect of a drug on the patient and comprising a cardiac rhythm management (CRM) device including one or more pacemakers or one or more cardioverter defibrillators;
   a communication network;
   a host including a database module, an analysis module, and a delivery module, the database module configured to receive and store the measured data through the communication network, the analysis module configured to compare the measured data to an expected pharmacodynamic model and to predict and determine issues or failures of the implantable device using the measured data, the delivery module configured to manage the implantable device through the communication network using the measured data, wherein the expected pharmacodynamic model is selected based on at least one characteristic of the patient selected from the group consisting of age, race, national origin, gender, and genetic factors;
   a device configured to provide an alert using an outcome of the comparison of the measured data and the expected pharmacodynamic model; and
   interrogator/transceiver units each including an interrogator configured to receive the measured data from the implantable device wirelessly and a transceiver configured to send the received measured data to the host through the communication network.

2. The system of claim 1, further comprising drug dispensers in communication with the interrogator/transceiver units, the drug dispensers each dispensing the drug and communicating a time that the drug is dispensed to the host.

3. The system of claim 2, wherein the drug dispensers comprise one or more implantable drug dispensers.

4. The system of claim 3, wherein the drug dispensers each dispense the drug based on a result of the comparison.

5. The system of claim 1, wherein the analysis module determines drug therapy regimen compliance based on a result of the comparison.

6. The system of claim 5, wherein the analysis module generates a compliance report based on the drug therapy regimen compliance.

7. The system of claim 1, wherein the analysis module identifies an unexpected effect based on a result of the comparison.

8. The system of claim 7, wherein the analysis module generates a side-effect report based on the unexpected effect.

9. The system of claim 7, wherein the analysis module generates a drug resistance report based on the unexpected effect.

10. The system of claim 7, wherein the analysis module generates an alarm based on the unexpected effect.

11. The system of claim 10, wherein the host communicates the alarm to the patient.

12. The system of claim 1, wherein the analysis module is configured to suggest modification of the drug therapy regimen based on a result of the comparison.

13. The system of claim 1, wherein the CRM device comprises the one or more pacemakers.

14. The system of claim 1, wherein the CRM device comprises the one or more cardioverter defibrillators.

15. The system of claim 1, wherein the pharmacological effect is at least one selected from the group consisting of activity level, weight, brachial and intracardiac or systemic blood pressure, heart rate, thoracic impedance, heart sounds, and heart rate variability.

16. The system of claim 1, wherein the analysis module creates the expected pharmacodynamic model for the patient based on the data measured.

17. The system of claim 1, wherein the analysis module automatically selects the expected pharmacodynamic model based on the data measured by the implantable device.

18. The system of claim 1, wherein the interrogator/transceiver units each comprise a hand-held device wirelessly coupled to the communication network.

19. The system of claim 1, further comprising an external device configured to measure and record subjective patient data.

20. The system of claim 1, wherein the analysis module comprises a patient analysis module configured to predict an oncoming event based on the measured data.

21. The system of claim 20, which delivers a therapy based on the predicted event.

22. The system of claim 21, wherein the event is a cardiovascular event.

23. The system of claim 1, further comprising a device configured to communicate with the implantable device and communicate with the patient using sound or visual prompts.

24. The system of claim 1, wherein the analysis module is configured to identify early degradation or imminent failure of the implantable device.

* * * * *